United States Patent [19]

Takahashi

[11] Patent Number: 5,128,613
[45] Date of Patent: Jul. 7, 1992

[54] METHOD OF INSPECTING MAGNETIC CARBURIZATION IN A NON-PERMEABLE MATERIAL AND PROBE THEREFORE

[75] Inventor: Makoto Takahashi, Osaka, Japan

[73] Assignee: Kubota Ltd., Osaka, Japan

[21] Appl. No.: 785,197

[22] Filed: Nov. 1, 1991

Related U.S. Application Data

[63] Continuation of Ser. No. 465,625, Jan. 19, 1990, abandoned, which is a continuation of Ser. No. 349,902, May 9, 1989, abandoned, which is a continuation of Ser. No. 289,460, Dec. 22, 1988, abandoned, which is a continuation of Ser. No. 832,199, Feb. 24, 1986, abandoned.

[30] Foreign Application Priority Data

| Feb. 25, 1985 | [JP] | Japan | 60-37191 |
| Jul. 2, 1985 | [JP] | Japan | 60-145972 |
| Jul. 2, 1985 | [JP] | Japan | 60-145974 |
| Jul. 2, 1985 | [JP] | Japan | 60-145975 |

[51] Int. Cl.$^5$ .................... G01N 27/87; G01N 33/12
[52] U.S. Cl. ................... 324/235; 324/225; 324/262
[58] Field of Search ........... 324/207.12, 207.13, 324/207.20, 209, 219, 220, 221, 225–229, 232–243, 251, 252, 260, 262; 307/309; 332/32 R, 32 H

[56] References Cited

U.S. PATENT DOCUMENTS

| 3,579,099 | 5/1971 | Kanbayashi | 324/235 |
| 3,609,530 | 9/1971 | Johnson | 324/210 |
| 3,689,828 | 9/1972 | Kurose et al. | 324/235 |
| 3,764,897 | 10/1973 | Greenwood | 324/233 X |
| 4,041,379 | 8/1977 | Karlsson | 324/242 X |
| 4,066,962 | 1/1978 | Jaffee | 324/235 X |
| 4,095,180 | 6/1978 | Brown | 324/233 |
| 4,095,181 | 6/1978 | Harris et al. | 324/238 |
| 4,121,288 | 10/1978 | Hickam | 324/213 X |
| 4,195,260 | 3/1980 | Sakamoto et al. | 324/236 X |
| 4,373,271 | 2/1983 | Nitz | 324/251 X |
| 4,406,272 | 9/1983 | Kiess et al. | 324/207.2 X |
| 4,468,619 | 8/1984 | Reeves | 324/235 X |
| 4,518,918 | 5/1985 | Avery | 338/32 H X |
| 4,524,932 | 6/1985 | Bodziak | 324/235 X |
| 4,535,289 | 8/1985 | Abe et al. | 324/235 X |
| 4,593,244 | 6/1986 | Summers et al. | 324/234 X |
| 4,870,360 | 9/1989 | Collins et al. | 324/235 |

FOREIGN PATENT DOCUMENTS

| 2025317 | 12/1970 | Fed. Rep. of Germany . |
| 51-123090 | 10/1976 | Japan . |
| 1261346 | 1/1972 | United Kingdom | 324/235 |
| 2012966 | 8/1979 | United Kingdom . |
| 1567166 | 5/1980 | United Kingdom . |

OTHER PUBLICATIONS

Napijalo et al. "Measurement of Magnetic Properties of Ferromagnetic Materials in Static Magnetic Fields", *Fizika (Yugoslaria) Conf.*, vol. 8, Suppl. 1976, pp. 31–34.

Bron et al. "Zond Automated Installation for Magnetic Inspection of the External Surface of Circular Hot–Rolled Stock", *Magnetic & Electromagnetic Methods*, (From Defektoskopia (S.U.) Nov. 9, Sep. 1978), Non Destructive Testing (U.S.A.), vol. 14, No. 9, May 1979, pp. 835–841.

*Primary Examiner*—Kenneth A. Wieder
*Assistant Examiner*—Warren S. Edmonds
*Attorney, Agent, or Firm*—Armstrong, Nikaido, Marmelstein, Kubovcik & Murray

[57] ABSTRACT

A probe comprises a magnet and a Hall element which are provided in a magnetically impermeable case. The Hall element is disposed at the midportion between the two poles of the magnet in parallel with the lines of magnetic force. The presence of a carburized portion in the member to be inspected and the depth of carburization are detected by passing d.c. current across the Hall element and detecting the Hall effect electromotive force produced between the two ends of the element which are opposed in a direction perpendicular to the direction of flow of the current.

5 Claims, 4 Drawing Sheets

METHOD OF INSPECTING MAGNETIC CARBURIZATION IN A NON-PERMEABLE MATERIAL AND PROBE THEREFORE

This application is a continuation of Ser. No. 465,625 filed Jan. 19, 1990 which in turn is a continuation of Ser. No. 349,902 filed May 9, 1989, which in turn is a continuation of Ser. No. 289,460 filed Dec. 22, 1988, which in turn is a continuation of Ser. No. 832,199 filed Feb. 24, 1986 all of which are now abandoned.

FIELD OF INDUSTRIAL APPLICATION

The present invention relates to a method of non-destructively inspecting from outside carburized portions developing on the surface of metal materials, for example, carburized portions occurring on the inner surface of a cracking tube for producing ethylene in the petrochemical industry, and to a probe useful for this method.

PRIOR ART

In the petrochemical industry, starting material naphtha is passed through a cracking tube and thermally cracked at a high temperature and high pressure within the tube to prepare ethylene or the like. Metal materials used for this cracking tube are ASTM HK40 (0.4% C - 25% Cr -20% Ni), HP45 (0.45% C - 25% Cr - 35% Ni), HP material having Mo, W, Nb or the like incorporated therein singly or in combination, etc. Both HK and HP materials are well known alloys having extremely low magnetic permeability. As such, these materials are regarded as being substantially magnetically non-permeable.

When the cracking tube is used for a long period of time, the carbon resulting from the reaction adheres to the inner surface of the tube and diffuses into the metal at a high temperature to cause carburization. The carbon introduced by carburization forms chromium carbides, which grow into coarse particles with the acceleration of carburization to result in seriously reduced ductility in a low temperature range (up to about 800° C.). The carburized portion of the tube is smaller than the other portion thereof in coefficient of expansion, so that when the tube is greatly heated or cooled rapidly, the resulting tensile or compression stress could break the tube which has reduced ductility in the low temperature range.

Accordingly, in order to prevent the break of the tube and assure a trouble-free safety operation, it is necessary to periodically check the tube properly for carburization or progress of carburization.

The check method heretofore used is limited only to the magnetic induction method wherein the tube to be checked is subjected to an alternating magnetic field to detect the inductive current due to variation in the magnetic flux density at a carburized portion.

However, the measurement of depth of carburization obtained by the magnetic induction method, when compared with the measurement obtained by destructive inspection, is in fairly close corresponding relation with the latter result in the case of tubes of HK40 but varies greatly and is therefore unreliable in the case of tubes of HP or improved HP materials.

This is attributable to the following reason. With tubes of HP or improved HP material, the tube material forms a decarburized and Cr-removed outer surface layer. The thickness of this layer increases with a rise in the temperature at which the tube is used, as well as with an increase in the period of use, to about 50 to about 500 μm. This portion has a higher magnetic permeability.

When such tubes are used for a prolonged period of time at a high temperature, the measurement indicating the decarburized layer on the outer surface is erroneously interpreted as indicating occurrence of carburization even if the tube inner surface is not carburized.

In checking the tube for carburization and the depth of carburization, therefore, it is presently necessary to evaluate the measurements obtained by removing the decarburized layer from the outer surface of the tube as by a grinder and thereafter checking the tube again. This can be done if the number of check portions is small, but if it is attempted to check a large number of portions, the method requires much time and involves many problems in practice.

The present inventor attempted to detect carburized portions with use of a probe incorporating a Hall element and connected to a gauss meter, by placing the probe on the outer surface of the tube to be inspected and measuring the residual magnetism released from the tube, since the carburized portion has an austenized metal structure, has increased magnetic permeability and retains residual magnetism by being influenced by earth magnetism or the like. However, the magnetic flux density of the carburized portion is too small (about 2 to about 3 gauss for HP material) and is slightly greater than that of the earth magnetism, so that the depth of carburization was not measurable accurately.

SUMMARY OF THE INVENTION

When the member to be inspected and having a carburized portion is subjected to a magnetic field by applying a magnetic-incorporated probe, the lines of magnetic force deflect toward the carburized portion. If a Hall element (Hall-effect device) is preliminarily disposed in parallel with the lines of magnetic force, the Hall element detects the disturbance of the magnetic flux to produce an intense output which can be distinguished from the earth magnetism.

An object of the present invention is to provide a method of manifestly detecting carburized portions in a magnetically non-permeable material, such as the HK and HP materials discussed above, with use of the combination of a Hall element and a magnet based on the above principle and to provide a probe for use in this method. As used in the specification and claims, the term "substantially magnetically non-permeable material" shall be understood to imply those materials having extremely low magnetic permeability on the order found in HK and HP materials.

Another object of the present invention is to provide a method of and a probe for detecting carburized portions without destroying the member to be inspected and almost without being influenced by a decarburized layer on the surface of the member.

Another object of the present invention is to provide a probe capable of detecting the spread of a carburized layer when the layer spreads over an area within the member to be inspected.

Another object of the present invention is to provide a probe for detecting a carburized layer without removing a decarburized layer and yet without being influenced by the decarburized layer even if the member to be inspected has the decarburized layer on its surface.

DETAILED DESCRIPTION OF THE INVENTION

Figure 1:
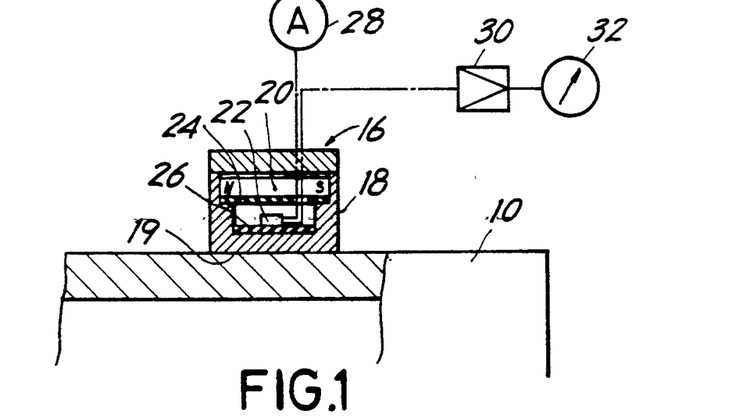
FIG. 1 is an overall diagram showing an embodiment of the invention during use.
Figure 2:
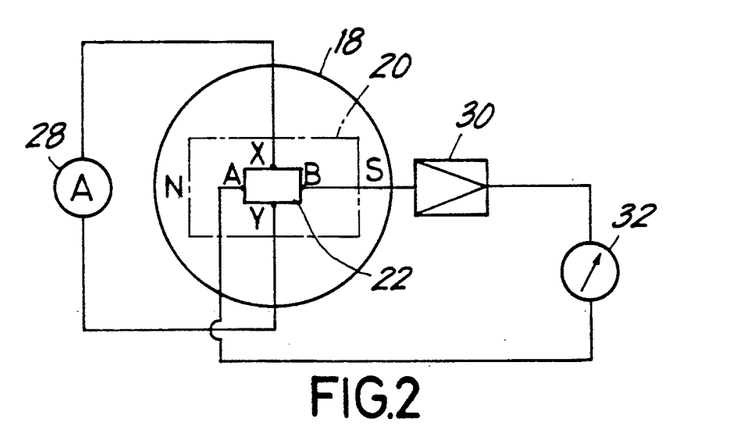
FIG. 2 is a diagram showing the circuit of the embodiment of FIG. 1.

FIGS. 1 and 2 show a probe 16 of the invention which includes a case 18 made of a magnetically impermeable material such as aluminum or synthetic resin, and an insulating plate 24 fitted in the case 18. A magnet 20 in the form of a permanent magnet or electromagnet is mounted on the insulating plate 24. A Hall element 22 is provided on an insulating plate 26 fitted in the bottom of the case 18. The magnet 20 is in a a horizontal position so that the magnetic field set up is substantially in parallel with an inspecting surface 19 of the case 18. The Hall element 22 is positioned usually horizontally in the same direction as the lines of magnetic force. The element 22 has two pairs of terminals X, Y and A, B. Of these, one pair X, Y is connected to a current source 28, which passes a constant current (about 4 mA) across the Hall element 22 in the X-Y direction.

The other pair of terminals A, B is arranged in a direction perpendicular to the X-Y direction and connected to an amplifier 30 and a measuring device 32 for detecting the Hall electromotive force occurring across the terminals A, B.

With the inspecting surface 19 placed on the surface of the member 10 to be inspected, the probe 16 is moved axially or circumferentially of the member 10. A carburized portion, if present in the interior of the member 10, can be recognized by detecting the Hall electromotive force produced between the terminals A and B with the measuring device 32.

Figure 3:
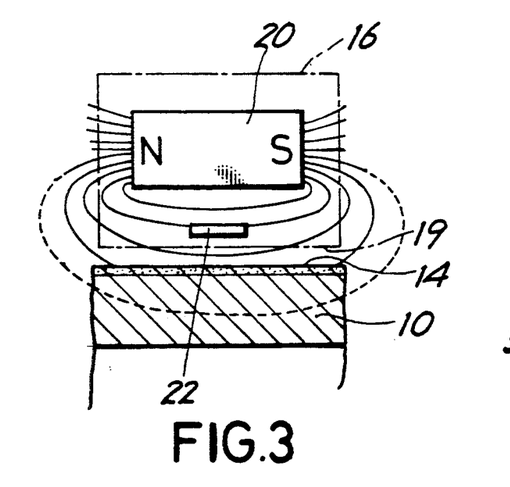
FIGS. 3 and 4 are diagrams showing a normal member and a member having a carburized portion to illustrate the deflection of lines of magnetic force due to the presence of the carburized portion.
Figure 5:
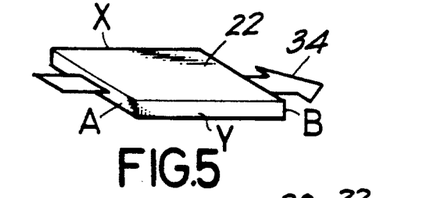
FIGS. 5 and 6 are diagrams showing the principle of the invention for detecting the carburized portion with a Hall element.

When the member 10 has no carburized portion, the lines of magnetic force of the magnet 20 are formed symmetrically and extend in the same direction as the plane of the Hall element 22, with no lines of magnetic force extending through the Hall element, so that even if current is passed across the opposite end terminals X and Y, no Hall electromotive force occurs across the output terminals A and B (see FIGS. 3 and 5).

Figure 4:
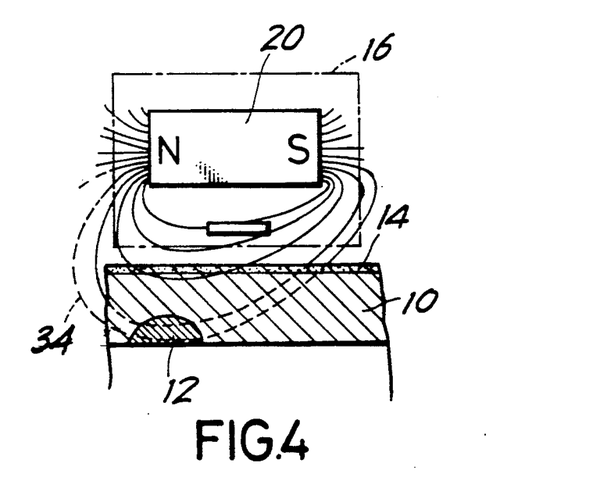
Figure 6:
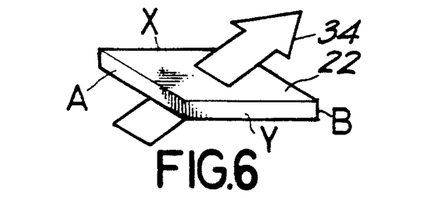

Nevertheless, if the member 10 has a carburized interior portion 12, the lines 34 of magnetic force of the magnet 20 deflect toward the carburized portion to disturb the magnetic field as shown in FIGS. 4 and 6 owing to the magnetic permeability of the carburized portion, so that the lines of magnetic force extending in the vicinity of the Hall element 22 incline, providing a perpendicular magnetic field component extending through the Hall element and producing a Hall electromotive force across the terminals A and B according to the density of magnetic flux through the surface of the element. When the magnetic field of the magnet 20 is given a sufficient strength, the lines of magnetic force through the Hall element 22 have a measurable magnitude even if the disturbance of the magnetic field due to the carburized portion is small. Thus, the carburized portion can be detected with high precision. Insofar as the Hall element is approximately parallel to the lines of magnetic force, carburized portions are detectable without any trouble even if the element is slightly inclined.

Figures 7, 24, 27:
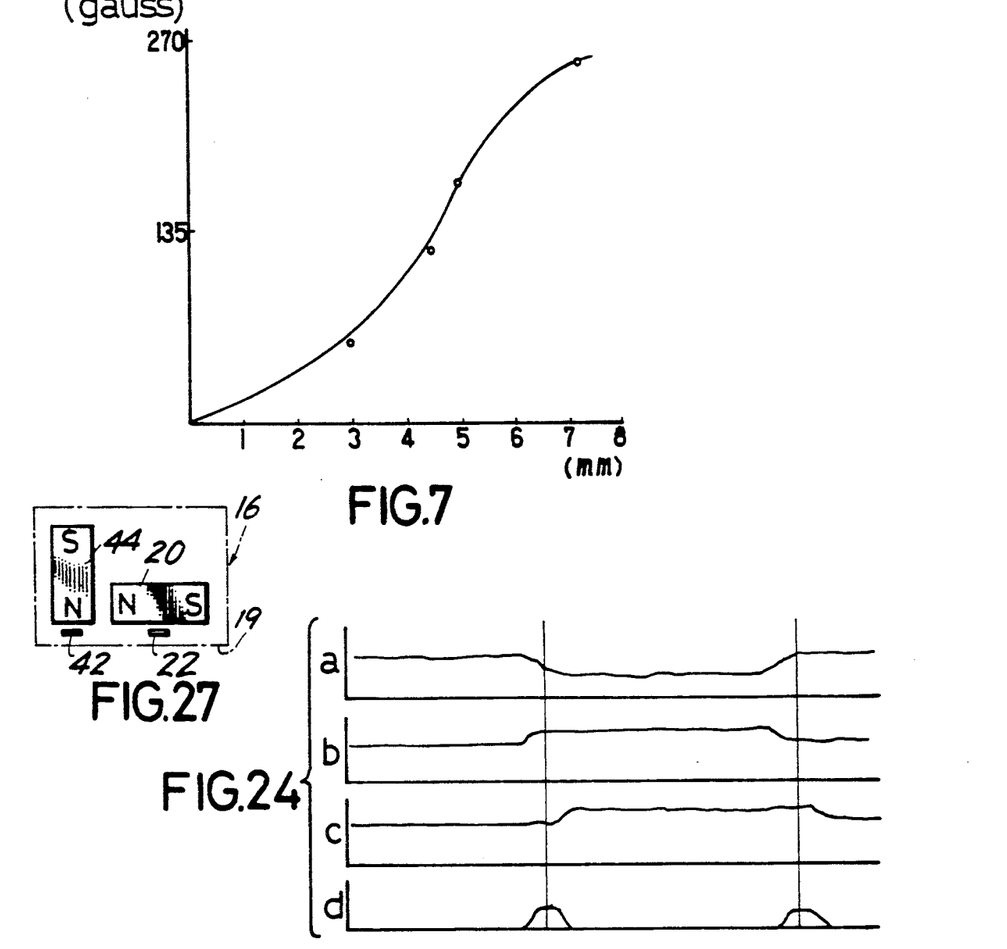
FIG. 7 is a graph showing the relation between the depth of carburization and the output of the Hall element.
FIG. 24, a to d, shows the output waveforms of the Hall elements of FIG. 23 and the waveform obtained by offsetting the outputs of the second and third Hall elements.
FIGS. 25 to 27 are front views showing other embodiments of the invention.
Figure 8:
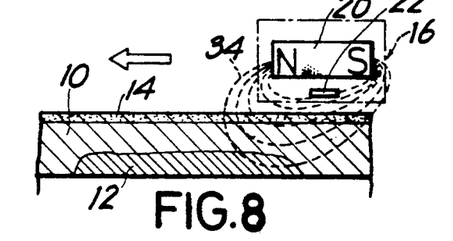
FIG. 8 is a front view showing the embodiment as used for detecting a spread carburized portion.

FIG. 7 shows the depths of carburized portions actually measured in comparison with the measurements obtained by checking the carburized portions with use of the probe of the invention having a gauss meter as the measuring device 32. The values obtained by the present probe are precisely in proportion to the actual depth measurements. This indicates that the present probe not only detects the presence of the carburized portion but also measures the depth of carburization. When the surface of the member to be inspected is covered with a decarburized layer 14, the layer is usually in the form of a thin layer of uniform thickness covering the entire surface of the member to be inspected. It can therefore be said that the decarburized layer extends almost indefinitely in every direction when compared with the size of the probe 16. Although the presence of the decarburized layer 14 results in an increased magnetic flux density because it is magnetically permeable, the layer produces no change in the symmetry of lines of magnetic force and causes no disturbance to the magnetic field. With no lines of magnetic force extending through the plane of the Hall element 22, there is no output electromotive force across the terminals A and B. Consequently, the carburized portion can be detected and measured free of the influence of the decarburized layer. When a plurality of probes are arranged on the surface of the member to be inspected and moved at the same time, the member can be checked over a wider area efficiently. The magnet can be in the form of a hollow cylinder, square tube or channel.

Figure 9:
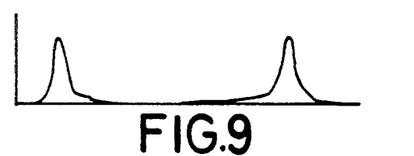
FIG. 9 is a diagram showing the waveform of the output of the Hall element.
Figure 10:
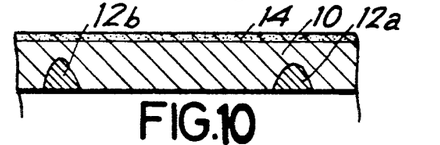
FIG. 10 is a sectional view showing the member to be inspected and having carburized portions in the form of spots.

When the probe of the construction shown in FIG. 1 is moved toward a carburized portion spreading over a large area, the lines of magnetic force, 34, deflect forward toward the direction of movement under the influence of the magnetic permeability of the carburized portion when the probe approaches the portion, while the lines of force deflect rearward when the probe moves past the carburized portion. However, while the probe is moving immediatley above the carburized portion 12, the carburized portion 12, which is sufficiently larger than the probe 16 (circular with a diameter of 20 mm), exerts a substantially uniform influence to cause no disturbance to the lines of magnetic force, which therefore become symmetric. Consequently, the Hall element 22 produces an output only at each end of the carburized portion 12 but gives no output at the intermediate part of the portion 12, as represented by the waveform of FIG. 9 having two peaks. This waveform resembles a waveform that would be obtained when detecting two local carburized portions 12a and 12b as seen in FIG. 10, and the two cases are not distinguishable from each other.

Figure 11:
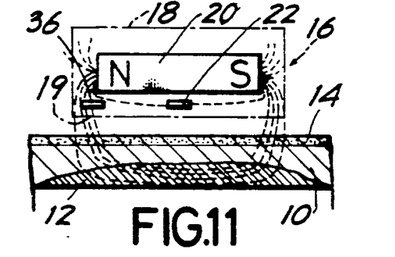
FIG. 11 is a front view showing another embodiment of the invention.

FIG. 11 shows an embodiment which is adapted to detect a widely spreading carburized portion 12 and measure the depth of carburization. This embodiment comprises two Hall elements 22 and 36. The first Hall element 22 is disposed at the midportion of a magnet along its magnetic field as in the first embodiment of FIG. 1. The second Hall element 36 is disposed close to one of the magnetic poles to intersect the magnetic field.

Figure 12:
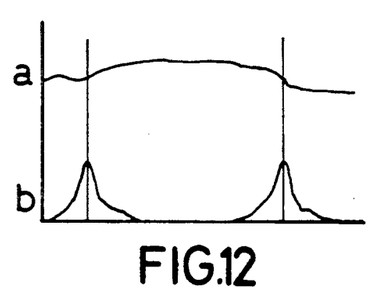
FIG. 12 is a diagram showing the output waveforms a and b of first and second Hall elements included in the embodiment of FIG. 11.

When the probe is moved past the spreading carburized portion 12, the first Hall element 22 exhibits a two-peak waveform b shown in FIG. 12.

While the second Hall element 36 produces a Hall electromotive force at all times due to lines of magnetic force penetrating through the element, the output increases progressively as the probe approaches the carburized portion 12 and remains increased while the probe is passing over the portion 12. The output gradually decreases when the probe is about to move past the portion 12. Accordingly, when the second Hall element 36 gives an increased output of the waveform a in FIG. 12, with the first Hall element 22 giving an output of two-peak waveform (FIG. 12, b), the part between the two peaks can be interpreted as indicating the spread of the carburized portion. Furthermor, the depth of carburization can be measured from the height of the waveform produced by the first Hall element 22.

Figure 13:
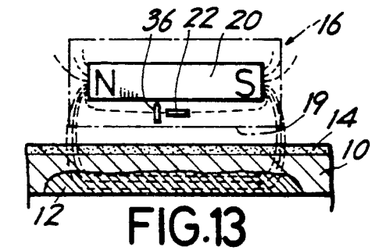
FIGS. 13 and 14 are front views showing other embodiments of the invention.
Figure 14:
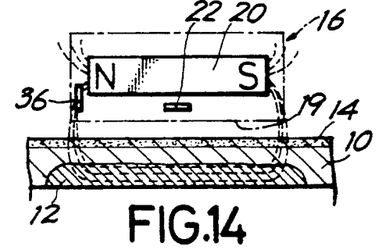

FIGS. 13 and 14 show other embodiments which are fabricated for the same purpose as the embodiment of FIG. 11. The components are the same as those shown in FIG. 11. With the embodiment of FIG. 13, the second Hall element 36 only is disposed to intersect the magnetic field at the midportion between the two magnetic poles.

Figure 15:
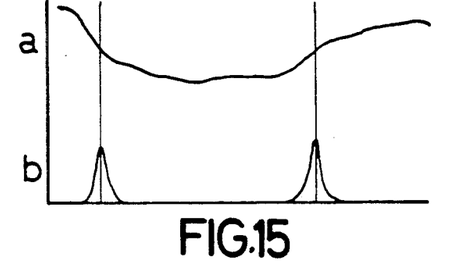
FIG. 15 is a diagram showing the output waveforms a and b of the Hall elements shown in each of FIGS. 13 and 14.

With the embodiment of FIG. 14, the second Hall element 36 is disposed in front of one magnetic pole to intersect lines of magnetic force, such that the number of intersecting lines of force decreases when the lines are deflected by the influence of a carburized portion. With either of the embodiments, when the probe moves over the carburized portion, lines of magnetic force are deflected toward the carburized portion, so that lines of force of force penetrate through the second Hall element 36, with a reduction in the density of lines through the second Hall element 36. Consequently, the second Hall element 36 produces a decreased output of waveform a in FIG. 15 while the probe passes over the carburized portion. Thus, the part between the two peaks of the waveform b produced by the first Hall element 22 indicates the spread of the carburized portion.

Figures 16, 17, 18, 20:
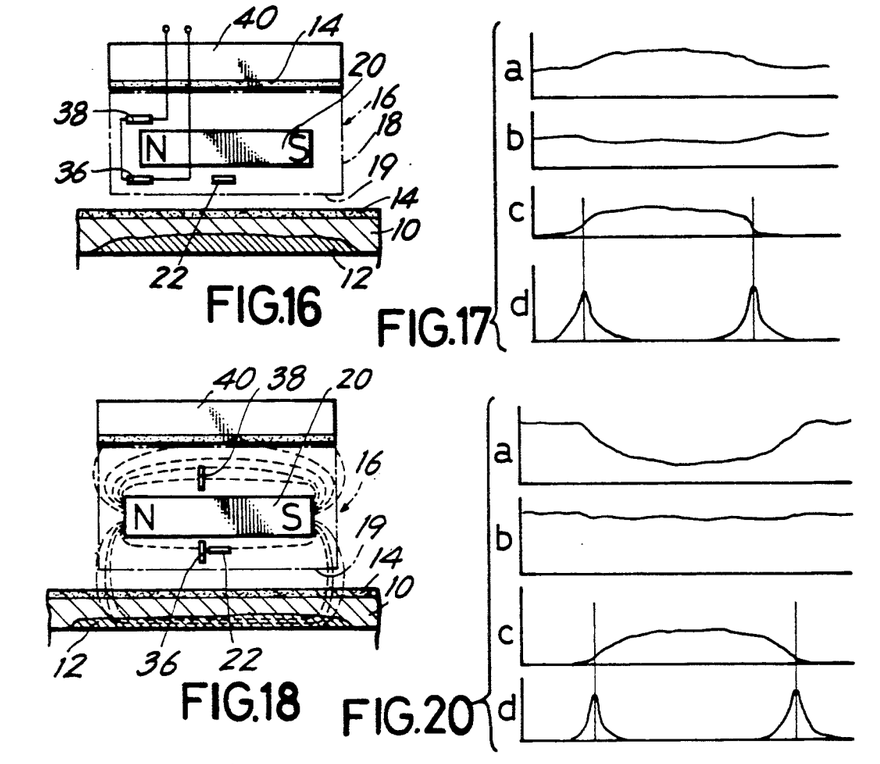
FIG. 16 is a front view showing another embodiment of the invention.
FIG. 17, a to d, shows the output waveforms of the Hall elements of FIG. 16 and the waveform obtained by offsetting the outputs of the second and third Hall elements.
FIGS. 18 and 19 are front views showing other embodiments of the invention.
FIG. 20, a to d, shows the output waveforms of the Hall elements of FIGS. 18 and 19 and the waveform obtained by offsetting the outputs of the second and third Hall elements.
Figure 19:
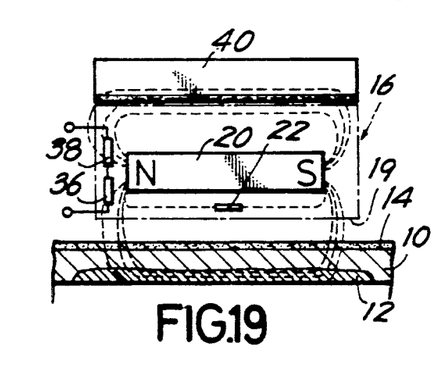

FIGS. 16, 18 and 19 show embodiments which overcome the problem of variations in the output of the second Hall element 36 due to the influence of a decarburized layer 14 on the surface of the member 10 to be inspected.

The embodiment of FIG. 16 has the same construction as the one shown in FIG. 11 except that a thrid Hall element 38 is disposed in the vicinity of the magnet 20 symmetrically with the second Hall element 36 and positioned in the magnetic field on the other side of the magnet. The second and third Hall elements are so reversely connected as to offset their outputs by each other, or the outputs of the two Hall elements are offset by being electrically processed by a subtraction device.

Removably mounted on the case 18 is a dummy piece 40 which is equivalent in magnetic permeability to the member 10 to be inspected and which is obtained by cutting off a carburization-free portion of the member 10 or prepared from other member. The position relation between the dummy piece 40 and the third Hall element 38 is in symmetry with the position relation between the member 10 and the second Hall element 36. When the surface of the member 10 is covered with a decarburized layer 14, the influence exerted on the second Hall element 36 by the member 10 including the decarburized layer 14 is equivalent to the influence exerted on the third Hall element 38 by the dummy piece 40.

When the probe 16 is moved over a carburized portion 12, the first Hall element 22 produces an output of waveform d in FIG. 17, the second Hall element 36 an output of waveform a in FIG. 17, and the third Hall element 38 an output of waveform b in FIG. 17 because the lines of magnetic force are entirely deflected toward the carburized portion to result in a slight reduction in the number of lines through the element 38.

When the outputs of the second and third Hall elements are offset, the waveform c of FIG. 17 is obtained, which is exclusive of the influence of the decarburized layer 14. The presence of the carburized portion 12 in the member 10 can therefore be detected with improved precision.

The embodiments of FIGS. 18 and 19 have the same construction as the embodiments of FIG. 16 in respect of the magnet 20, first Hall element 22 and dummay piece 40 but differ therefrom in the arrangement of the second and third Hall elements.

With the embodiment of FIG. 18, the second Hall element 36 and the third Hall element 38 are arranged at the midpoint of the magnet 20 symmetrically with respect thereto to intersect lines of magnetic force.

With the embodiment of FIG. 19, the second and third Hall elements 36 and 38 are arranged in front of one magnetic pole of the magnet 20 to intersect lines of magnetic force, such that when the magnetic field is deflected by the influence of a carburized portion 12, the density of the intersecting magnetic flux decreases.

With either of the above embodiments, when the lines of magnetic force are greatly deflected toward the carburized portion owing to the movement of the probe 16 above the carburized portion 12, the number of lines of magnetic force intersecting the second and third Hall elements 36 and 38 decreases. Especially, the second Hall element, which is positioned toward the inspection surface 19 of the probe 16, is greatly influenced by the disturbed lines of force, producing an output of waveform a shown in FIG. 20.

On the other hand, the third Hall element 38, which is disposed on the other side of the second Hall element 36 opposite to the member 10 symmetrically with the element 36, is less influenced by the disturbance of lines of magnetic force due to the presence of the carburized portion 12 and therefor exhibits the waveform b of FIG. 20. Accordingly, by offsetting the outputs of the second and third Hall elements, the waveform c of FIG. 20 is obtained which is free of the influence of the decarburized layer 14 and which indicates the presence of the carburized portion 12. With reference to this waveform and the two-peak waveform d of FIG. 20 produced by the first Hall element 22, the presence of the carburized portion 12 can be detected, and the depth of carburization measured.

Figure 21:
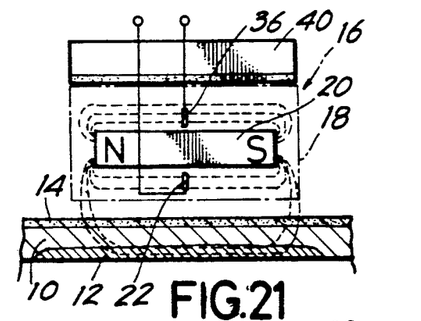
FIGS. 21 and 22 are front views showing other embodiments of the invention.
Figure 22:
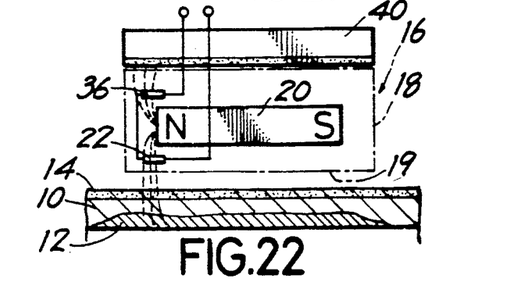

FIGS. 21 and 22 show other embodiments of the invention. With reference to FIG. 21, the probe has a dummy piece 40 on its case 18, and first and second Hall elements 22 and 36 which are arranged at the midportion between two magnetic poles symmetrically with respect to the magnet 20 to intersect lines of magnetic force. The first and second Hall elements 22 and 36, always intersecting the lines of magnetic force, produce Hall electromotive forces of equal intensities. However, when the probe is moved above a carburized portion 12, the lines of force are attracted toward the portion 12. This greatly influences the density of magnetic flux through the first Hall element 22 to reduce the density but less influences the density of magnetic flux through the second Hall element 36 since it is away from the carburized portion 12. The influence of a decarburized layer 14 is eliminated by offsetting the outputs of the two Hall elements, enabling the probe to detect the presence of the carburized portion 12 and measure the depth of carburization.

When the probe of FIG. 22 is moved above a carburized portion 12, the density of magnetic flux through the first Hall element 22 greatly increases since the flux is attracted toward the portion 12, whereas the variation in the density of magnetic flux through the second Hall element 36 is small. By offsetting the outputs of the two Hall elements, an output waveform is obtained which indicates the influence of the carburized portion 12 on the density of magnetic flux through the first Hall element.

Figure 23:
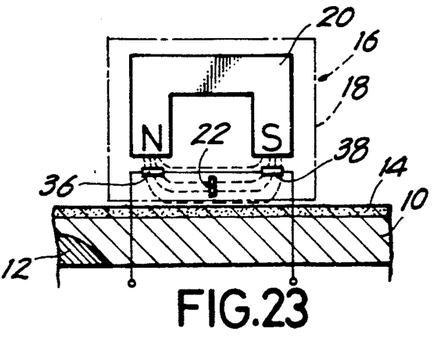
FIG. 23 is a front view showing another embodiment of the invention.

FIG. 23 shows an embodiment which comprises a channel-shaped magnet 20, a first Hall element 22 disposed at the midportion between the two magnetic poles and intersecting lines of magnetic force, and second and third Hall elements 36, 38 disposed close to the two poles respectively symmetrically and intersecting lines of force. When the probe 16 is moved above a carburized portion 12, the lines of magnetic force are attracted toward the portion 12 which is highly magnetically permeable to reduce the density of magnetic flux through the first Hall element 22 and increase the density of flux through the second and third Hall elements 36, 38.

FIG. 24 shows the Hall effect output waveforms a, b and c produced by the first element 22, second element 36 and third element 38, respectively. With respect to the direction of advance of the probe 16, the second Hall element 36 precedes the third Hall element 38 in phase, so that when the outputs of the second and third Hall elements are offset, a waveform is obtained which has two peaks corresponding to the opposite ends of the carburized portion as indicated at a in FIG. 24. With reference to this waveform and the waveform a of FIG. 24, the spread of the carburized portion can be detected.

In the case of this embodiment, the second and third Hall elements 36, 38 are similarly subjected to the influence of a decarburized layer 14 on the member 10 to be inspected. Accordingly, the influence of the decarburized layer 14 can be eliminated by offsetting the outputs of these two elements without the necessity of providing the dummy piece unlike other embodiments.

Figure 25:
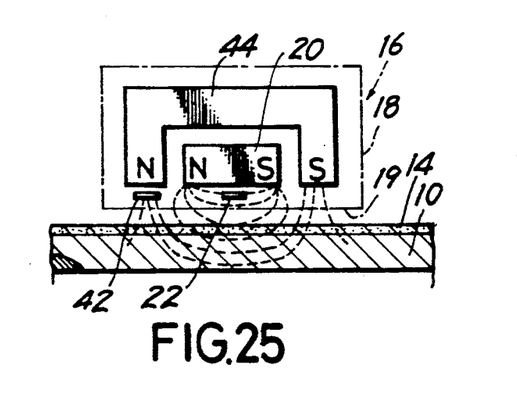

FIG. 25 shows another embodiment of the invention which comprises a magnet 20 and a channel-shaped second magnet 44 disposed outside the magnet 20. The two magnets are arranged within a case 18 with like poles opposed to each other. A first Hall element 22 is displaced at the midportion of the magnet 20 along the lines of magnetic force. The lines of magnetic force emitted by the opposed like poles of the two magnets repel each other and penetrate deep into the member 10 to be inspected. The probe is therefore advantageous for checking members having a large thickness. Provided in the vicinity of one pole of the second magnet 44 is a magnetic sensor 42 for detecting variations in the flux density of the second magnet 44. The sensor 42 shown in FIG. 25 is a Hall element so disposed as to intersect lines of magnetic force. The sensor 42 shown in FIG. 26 is a mutual induction coil.

The probe shown in FIG. 27 comprises a second magnet 44 in the form of a bar magnet and disposed at a right angle with first magnet 20, with like poles opposed to each other. The first magnet, as well as the second, can be in the form of a solid body, hollow cylinder or square to rectangular tube.

Figure 26:
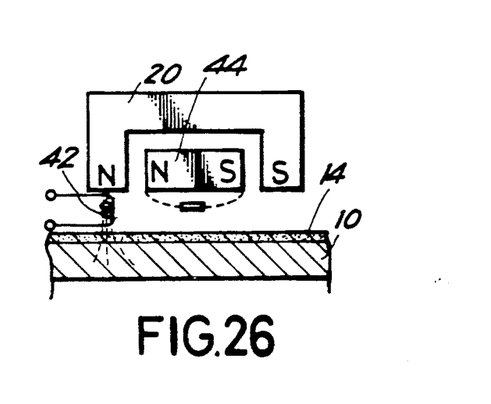

With any of the embodiments of FIG. 25 to 27, the density of magnetic flux emitted by the second magnet 44 increases in the vicinity of a carburized portion. Accordingly, spread carburized portions can be detected and the depth of carburation measured by detecting the increase in the flux density by the sensor 42.

Although the present invention has been described above specifically with reference to the embodiments shown in the drawings, various modifications can of course be made by one skilled in the art without departing from the spirit of the invention as defined in the appended claims in practing the invention.

What is claimed is:

1. An apparatus for detecting carburization in an object to be inspected comprising a substantially magnetically non-permeable material comprising:
   a probe comprising:
   a casing made of a non-magnetic test material,
   a magnet positioned in the casing and emitting lines of magnetic force toward an inspection side of the casing, the poles of said magnet pointing in a direction parallel to said inspection side,
   a first Hall element placed in the casing between the magnet and the inspection side of the casing and being disposed in a field of and parallel to the lines of magnetic force, a second Hall element being disposed at the midportion between the two magnetic poles of the magnet to intersect the lines of magnetic force so as to detect a decrease of the density of magnetic flux through the second Hall element when the magnet approaches a carburized portion in said magnetically non-permeable material;

wherein each of the first and second Hall elements has a pair of terminals connectable to a current source for passing d.c. current therethrough and another pair of terminals connectable to a measuring device for detecting a Hall electromotive force, and wherein during inspection of said object the first Hall element remains unchanged and the second Hall element emanates a high output signal in its normal state, whereas the first Hall element emanates an output signal by detecting an inclination of the lines of magnetic force, said inclination being caused by a disturbance of the magnetic flux toward a carburized portion in said magnetically non-permeable material and the second Hall element decreases said high output signal when the probe is passed over a carburized portion in the magnetically non-permeable material.

2. An apparatus as defined in claim 1 wherein said probe further comprises a third Hall element disposed symmetrically with the second Hall element with respect to the magnet, and a dummy piece approximately equivalent in magnetic permeability to said substantially magnetically non-permeable material is disposed oppositely to the third Hall element and approximately symmetrically with the position of the object to be inspected relative to the second Hall element, wherein the Hall electromotive forces of the second Hall element and the third Hall element are offset to detect the carburized portion in said magnetically non-permeable material.

3. An apparatus for detecting carburization in an object to be inspected comprising a substantially magnetically non-permeable material comprising:
  a probe comprising:
  a casing made of a non-magnetic material,
  a magnet positioned in the casing and emitting lines of magnetic force toward an inspection side of the casing, the poles of said magnet pointing in a direction parallel to said inspection side,
  a Hall element positioned in the casing between the magnet and the inspection side of the casing and being disposed in a field of and parallel to the lines of magnetic force,
  the Hall elements containing a pair of terminals connectable to a current source for passing d.c. current therethrough and another pair of terminals connectable to a measuring device for detecting a Hall electromotive force;

wherein during inspection of said object the Hall element remains unchanged in the field of lines of magnetic force in its normal state, but the Hall element emanates an output signal when it detects an inclination of the lines of magnetic force, said inclination being caused by a disturbance of the magnetic flux toward a carburized portion of the magnetically non-permeable material.

4. An apparatus for detecting carburization in an object to be inspected comprising a substantially magnetically non-permeable material comprising:
  a probe comprising:
  a casing made of non-magnetic test material, a magnet positioned in the casing and emitting lines of magnetic force toward an inspection side of the casing, the poles of said magnet pointing in a direction parallel to said inspection side,
  a first Hall element disposed at the midportion between the two magnetic poles of the magnet to intersect the lines of magnetic force so as to detect a decrease of the density of the magnetic flux through the first Hall element when the magnet approaches a carburized portion, said decrease being the result of a disturbance of the magnetic flux caused by the carburized portion,
  a second Hall element positioned symmetrically with the first Hall element with respect to the magnet to intersect lines of magnetic force emitted toward a side of the casing opposite to the inspection side, and
  a dummy piece approximately equivalent in magnetic permeability to said magnetically non-permeable material, the dummy piece being positioned at a position opposite the inspection side of the casing adjacent to the second Hall element, the first and second Hall elements having a pair of terminals connectable to a cuurent source for passing d.c. current therethrough and another pair of terminals connectable to a measuring device for detecting a Hall electromotive force;

wherein the Hall electromotive forces of the first Hall element and the second Hall element are offset to detect a carburized portion in said magnetically non-permeable material.

5. A method for detecting carburization in a substantially magnetically non-permeable material comprising the steps of:
  creating lines of magnetic force by a magnet;
  positioning the magnet in a fixed position close to a Hall element so that said Hall element is disposed parallel to the lines of magnetic force and the lines of magnetic force pass tangentially along the Hall element without intersecting the Hall element;
  passing the magnet and the Hall element over the substantially magnetically non-permeable material to be inspected for carburization, wherein the Hall element is disposed between the magnet and the magnetically non-permeable material being inspected, thereby causing lines of magnetic force to pass through the material; and
  generating a signal by the Hall element when the line of magnetic force intersect a carburized portion of the magnetically non-permeable material thereby causing the lines of magnetic force to incline and to intersect the Hall element.

* * * * *

UNITED STATES PATENT AND TRADEMARK OFFICE
CERTIFICATE OF CORRECTION

PATENT NO. : 5,128,613

DATED : July 7, 1992

INVENTOR(S) : Makoto TAKAHASHI

It is certified that error appears in the above-identified patent and that said Letters Patent is hereby corrected as shown below:

On the title page, Item [30], please add the following priority data information:

--July 2, 1985 [JP] 60-145977
  July 2, 1985 [JP] 60-145978--

Signed and Sealed this

Seventeenth Day of August, 1993

Attest:

BRUCE LEHMAN

Attesting Officer  Commissioner of Patents and Trademarks